United States Patent
Ruben et al.

(10) Patent No.: US 12,082,354 B2
(45) Date of Patent: Sep. 3, 2024

(54) ELECTRONIC PACKAGE AND DEVICE INCLUDING SAME

(71) Applicant: Medtronic, Inc., Minneapolis, MN (US)

(72) Inventors: David A. Ruben, Mesa, AZ (US); Andrew J. Ries, Lino Lakes, MN (US); Pankti N. Shah, Phoenix, AZ (US); Jason D. Hamack, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 414 days.

(21) Appl. No.: 17/574,362

(22) Filed: Jan. 12, 2022

(65) Prior Publication Data
US 2022/0248545 A1      Aug. 4, 2022

Related U.S. Application Data

(60) Provisional application No. 63/143,990, filed on Feb. 1, 2021.

(51) Int. Cl.
*H05K 5/00*      (2006.01)
*A61N 1/378*    (2006.01)
(Continued)

(52) U.S. Cl.
CPC ......... *H05K 5/0095* (2013.01); *A61N 1/3787* (2013.01); *H02J 50/10* (2016.02);
(Continued)

(58) Field of Classification Search
CPC ............... H05K 5/0095; H05K 5/0052; H05K 2201/10015; H02J 50/10; A61N 1/3787; H02K 1/181
See application file for complete search history.

(56) References Cited

U.S. PATENT DOCUMENTS 8,805,537 B1 *   8/2014  Cong ................... A61N 1/3758
                                                                 607/116
10,124,559 B2   11/2018  Sandlin et al.
(Continued)

FOREIGN PATENT DOCUMENTS

EP            2428486       3/2012
WO       2020208481      10/2020

OTHER PUBLICATIONS

PCT/US2022/014481 filed Jan. 31, 2022; International Search Report and Written Opinion mailed May 12, 2022; 11 pages.
(Continued)

*Primary Examiner* — Jared Fureman
*Assistant Examiner* — Duc M Pham
(74) *Attorney, Agent, or Firm* — Mueting Raasch Group

(57) ABSTRACT

Various embodiments of an electronic package and implantable medical device are disclosed. The electronic package includes a nonconductive substrate having a first major surface, a second major surface, and an opening disposed through the substrate between the first major surface and the second major surface. The package also includes a conductive layer hermetically sealed to the first major surface of the substrate and over the opening; a conductor block disposed in the opening and extending beyond the second major surface of the substrate, where the conductor block is electrically connected to the conductive layer; and an electronic device disposed adjacent to the first major surface of the substrate and electrically connected to the conductive layer. The package also includes a nonconductive cover disposed over the electronic device and the nonconductive substrate and hermetically sealed to the substrate, where the electronic device is disposed within a cavity of the cover.

20 Claims, 9 Drawing Sheets

(51) Int. Cl.
  *H02J 50/10* (2016.01)
  *H05K 1/18* (2006.01)
(52) U.S. Cl.
  CPC ........... *H05K 1/181* (2013.01); *H05K 5/0052* (2013.01); *H05K 2201/10015* (2013.01)

(56) References Cited

U.S. PATENT DOCUMENTS

| | | |
|---|---|---|
| 10,143,788 B2 | 12/2018 | Rudser et al. |
| 11,647,600 B2* | 5/2023 | Nielsen ................ H05K 7/1417 438/107 |
| 2014/0335301 A1 | 11/2014 | Van 'T Oever et al. |
| 2021/0143056 A1* | 5/2021 | Zhu ................... H01L 21/76807 |
| 2021/0296219 A1* | 9/2021 | Yen ......................... H01L 24/29 |

OTHER PUBLICATIONS

Au et al., "Thermal evaluation of a hermetic transcutaneous energy transfer system to power mechanical circulatory support devices in destination therapy" Sep. 2020 Artificial Organs 44(9): 955-967.

* cited by examiner

ELECTRONIC PACKAGE AND DEVICE INCLUDING SAME

RELATED PATENT APPLICATION

This application claims the benefit of U.S. Provisional Patent Application Ser. No. 63/143,990, filed on Feb. 1, 2021, which is incorporated by reference herein in its entirety.

TECHNICAL FIELD

This disclosure generally relates to an electronic package and in particular an implantable medical device that includes the electronic package.

BACKGROUND

Various systems require electrical coupling between electrical devices disposed within a sealed enclosure or housing and devices or systems external to the enclosure. Oftentimes, such electrical coupling needs to withstand various environmental factors such that a conductive pathway or pathways from the external surface of the enclosure to within the enclosure remains stable. For example, implantable medical devices (IMDs), e.g., cardiac pacemakers, defibrillators, neurostimulators, and drug pumps, which include electronic circuitry and one or more power sources, require an enclosure or housing to contain and seal these elements within a body of a patient. Many of these IMDs include one or more electrical feedthroughs to provide electrical connections between the elements contained within the housing and components of the IMD external to the housing, for example, one or more conductors, sensors, electrodes, and lead wires mounted on an exterior surface of the housing, or electrical contacts housed within a connector header, which is mounted on the housing to provide coupling for one or more implantable leads.

Transcutaneous energy transfer (TET) systems are used to supply power to implantable medical devices such as pumps that are implanted within a human body. An electromagnetic field generated by a transmitting coil outside the body can transmit power across a cutaneous (skin) barrier to a magnetic receiving coil implanted within the body. The receiving coil can then transfer the received power to the implanted pump or other implantable devices and to one or more power sources (e.g., batteries) implanted within the body to charge the power source. Such systems efficiently generate and wirelessly transmit a sufficient amount of energy to power one or more implanted devices while maintaining the system's efficiency and overall convenience of user.

TET systems can be utilized, e.g., with ventricular assist devices (VADs) that include implantable blood pumps that are used when a patient's heart is unable to provide adequate circulation to the patient's body, thereby leading to heart failure. Such patients may use a VAD while awaiting a heart transplant or for longer periods of time. Further, some patients may use a VAD while recovering from heart surgery. Such VADs typically include implanted power sources that can be charged, e.g., by a TET system.

SUMMARY

The techniques of this disclosure generally relate to an electronic package and an implantable medical device that includes such electronic package. The package can include a nonconductive substrate and a conductive layer hermetically sealed to a first major surface of the substrate over an opening disposed through the substrate. The package can also include a conductor block disposed in the opening of the substrate that is electrically connected to the conductive layer, and an electronic device disposed adjacent to the first major surface of the substrate and electrically connected to the conductive layer. A nonconductive cover can be disposed over the electronic device and the nonconductive substrate such that the electronic device is disposed within a cavity of the cover. The cover can be sealed to the substrate.

In one example, aspects of this disclosure relate to an electronic package that includes a nonconductive substrate having a first major surface, a second major surface, and an opening disposed through the substrate between the first major surface and the second major surface. The package also includes a conductive layer hermetically sealed to the first major surface of the substrate and over the opening; a conductor block disposed in the opening and extending beyond the second major surface of the substrate, where the conductor block is electrically connected to the conductive layer; and an electronic device disposed adjacent to the first major surface of the substrate and electrically connected to the conductive layer. The package also includes a nonconductive cover disposed over the electronic device and the nonconductive substrate and hermetically sealed to the substrate, where the electronic device is disposed within a cavity of the cover.

In another example, aspects of this disclosure relate to an implantable medical device that includes a housing and an electronic package disposed within the housing. The electronic package includes a nonconductive substrate having a first major surface, a second major surface, and an opening disposed through the substrate between the first major surface and the second major surface. The package further includes a conductive layer hermetically sealed to the first major surface of the substrate and over the opening; a conductor block disposed in the opening and extending beyond the second major surface of the substrate, where the conductor block is electrically connected to the conductive layer; and an electronic device disposed adjacent to the first major surface of the substrate and electrically connected to the conductive layer. The package further includes a nonconductive cover disposed over the electronic device and the nonconductive substrate and hermetically sealed to the substrate, where the electronic device is disposed within a cavity of the cover.

In another example, aspects of this disclosure relate to a method that includes disposing an opening through a nonconductive substrate, where the opening extends between a first major surface and a second major surface of the nonconductive substrate; hermetically sealing a conductive layer to the first major surface of the substrate and over the opening; and disposing a conductor block in the opening such that it extends beyond the second major surface of the substrate, where the conductor block is electrically connected to the conductive layer. The method further includes disposing an electronic device adjacent to the first major surface of the nonconductive substrate, where the electronic device is electrically connected to the conductive layer; disposing a nonconductive cover over the electronic device and the conductive layer, where the electronic device is disposed within a cavity of the cover; and hermetically sealing the nonconductive cover to the nonconductive substrate to form an electronic package.

In another example, aspects of this disclosure relate to a method that includes disposing an opening through a nonconductive substrate wafer such that the opening extends between a first major surface and a second major surface of the nonconductive substrate wafer; hermetically sealing a conductive layer to the first major surface of the nonconductive substrate wafer; and patterning the conductive layer. The method further includes disposing a conductor block in the opening of the nonconductive substrate wafer such that it extends beyond the second major surface of the nonconductive substrate wafer, where the conductor block is electrically connected to the conductive layer; disposing an electronic device adjacent to the first major surface of the nonconductive substrate wafer, where the electronic device is electrically connected to the conductive layer; and disposing a nonconductive cover wafer over the electronic device and the conductive layer, where the electronic device is disposed within a cavity of the nonconductive cover wafer. The method further includes hermetically sealing the nonconductive cover wafer to the nonconductive substrate wafer, and singulating the nonconductive cover wafer and the nonconductive substrate wafer to form an electronic package.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
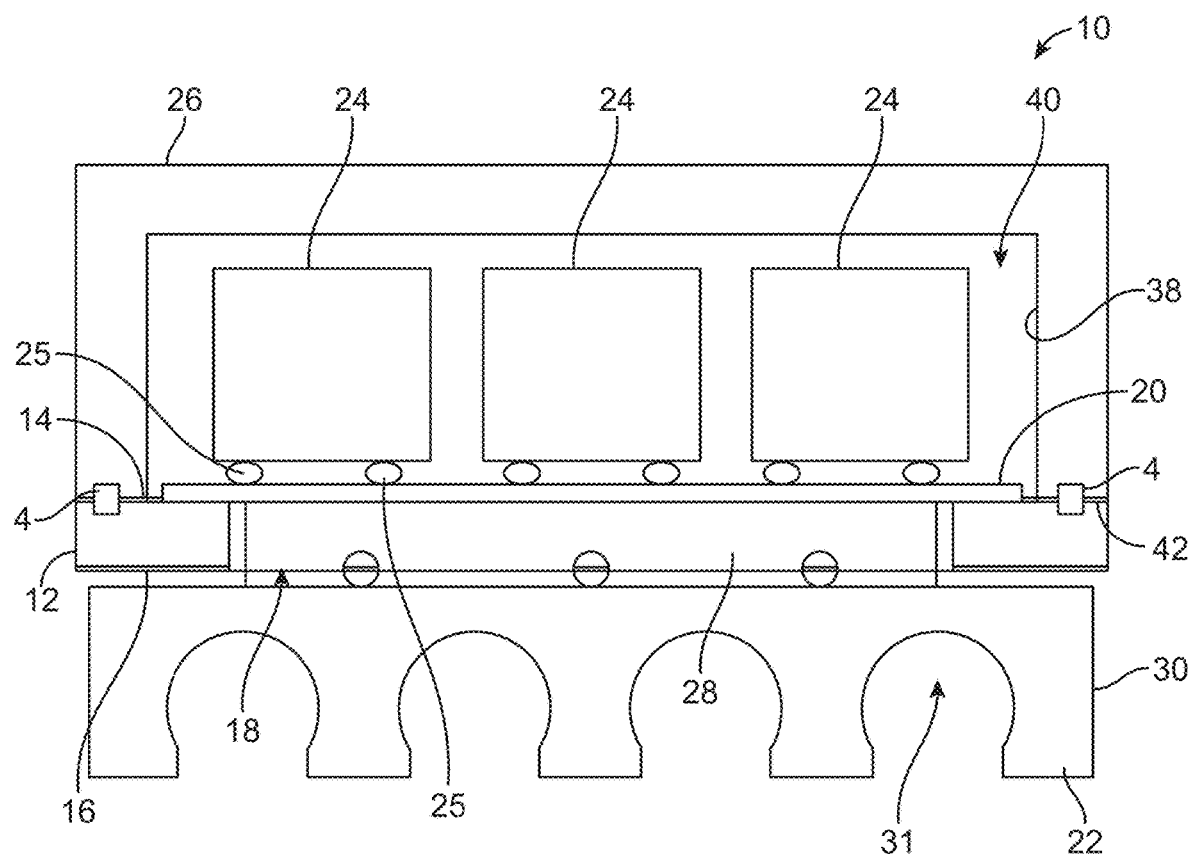
FIG. 1 is a schematic cross-section view of one embodiment of an electronic package.
Figure 2:
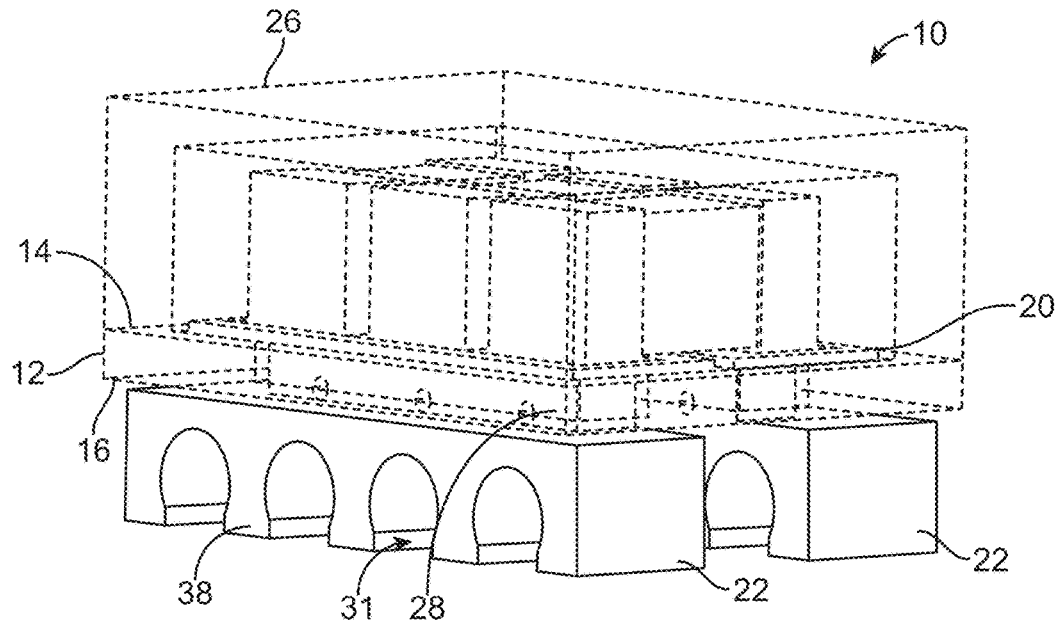
FIG. 2 is a schematic side perspective of the electronic package of FIG. 1 with a cover and a substrate of the package made transparent for clarity.
Figure 3:
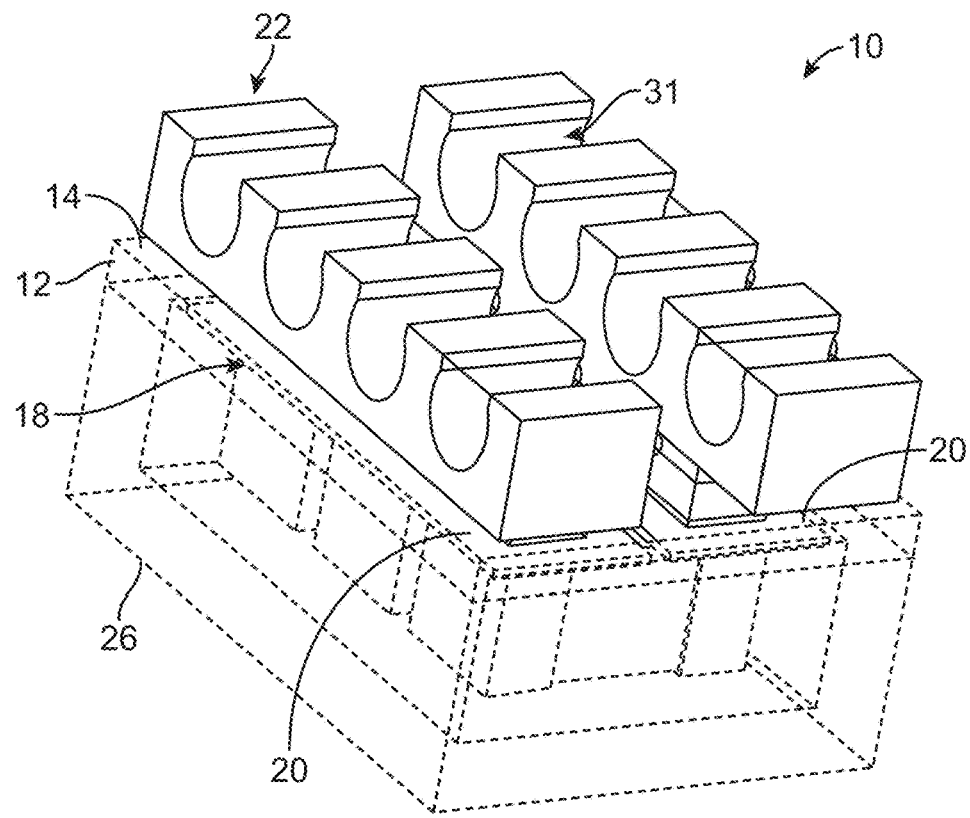
FIG. 3 is a schematic bottom perspective view of the electronic package of FIG. 1 with the cover and the substrate of the package made transparent for clarity.
Figure 4:
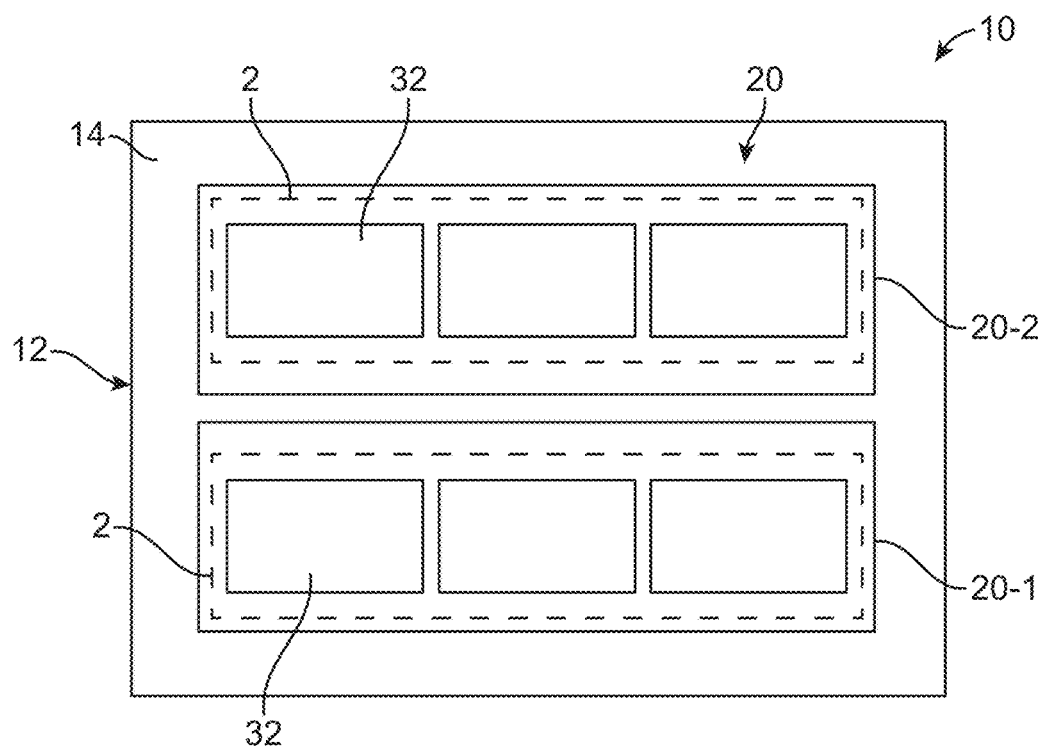
FIG. 4 is a schematic plan view of a first major surface of the substrate of the electronic package of FIG. 1.

The techniques of this disclosure generally relate to an electronic package and an implantable medical device that includes such electronic package. The package can include a nonconductive substrate and a conductive layer hermetically sealed to a first major surface of the substrate over an opening disposed through the substrate. The package can also include a conductor block disposed in the opening of the substrate that is electrically connected to the conductive layer, and an electronic device disposed adjacent to the first major surface of the substrate and electrically connected to the conductive layer. A nonconductive cover can be disposed over the electronic device and the nonconductive substrate such that the electronic device is disposed within a cavity of the cover. The cover can be sealed to the substrate.

Charging systems such as transcutaneous energy transfer systems can charge implantable medical devices by generating an electromagnetic field using an external transmitting coil and transmitting such field to a magnetic receiving coil implanted within a body of a patient and electrically connected to the implantable medical device. Such electromagnetic field can, however, undesirably produce eddy currents in portions of a housing of these implantable medical devices. Further, some housings of these implantable medical devices can reduce charging efficiency by interfering with the transmission of the electromagnetic radiation. Excessive heat can also be generated in metal materials of the housing or such materials disposed within the housing. Some housings of these systems can also lack hermeticity.

Various embodiments of electronic packages and devices and systems that include such packages provide one or more advantages over currently-available packages and devices. For example, one or more embodiments of packages described herein include a feedthrough that has low resistance such that large electrical currents can pass from a conductor block disposed external to a housing of the device to one or more electrical components disposed within the housing. Low resistance can be provided by the direct connection between the conductor block and the conductive layer. Further, one or more embodiments include a nonconductive housing that can reduce eddy-current formation in the housing when the package is exposed to an electromagnetic field used to charge the device. The package can have a low profile with a small form factor. Further, one or more embodiments of packages described herein can be manufactured using a wafer to wafer process.

FIGS. 1-5 are various views of one embodiment of an electronic package 10. The package 10 includes a substrate 12 that has a first major surface 14, a second major surface 16, and one or more openings 18 disposed through the substrate between the first major surface and the second major surface. The package 10 also includes one or more conductive layers 20 sealed to the first major surface 14 of the substrate 12 and over the opening 18; one or more conductor blocks 22 disposed in the openings and extending beyond the second major surface of the substrate, where the conductor blocks are electrically connected to the conductive layers; and one or more electronic devices 24 disposed adjacent to the first major surface of the substrate and electrically connected to the conductive layers. Further, the package 10 includes a cover 26 disposed over the electronic devices 24 and the substrate 12 and sealed to the substrate, where the electronic devices are disposed within a cavity 40 of the cover.

The substrate 12 can include any suitable material or materials. In one or more embodiments, the substrate 12 can be a nonconductive substrate that includes any suitable nonconductive material or materials, e.g., sapphire, glass, ceramic, etc. Further, the substrate 12 can take any suitable shape or shapes and have any suitable dimensions. As shown in FIG. 1, the first major surface 14 of the substrate 12 faces the electronic devices 24 and the cover 26, and the second major surface 16 faces the conductor blocks 22. Although depicted as including a single layer, the substrate 12 can include any suitable number of layers of the same material or differing materials. Further, the substrate 12 can be manufactured as a single part or singulated from a wafer as is further described herein.

Disposed through the substrate 12 between the first and second major surfaces 14, 16 are openings 18. Such openings 18 can have any suitable dimensions. Further, the openings 18 can take any suitable shape or shapes in a plane parallel to the first major surface 14 of the substrate, e.g., rectilinear, ovular, polygonal, etc. Any suitable number of openings 18 can be disposed through the substrate 12, e.g., one, two, three, four, five, or more openings. The openings 18 can be disposed through the substrate 12 using any suitable technique or techniques, e.g., grit blasting, mechanical machining, laser drilling, chemical etching, water jet, etc.

The conductive layer 20 can be disposed on the first major surface 14 of the substrate 12 and over one or more of the openings 18. In one or more embodiments, the conductive layer 20 occludes one or more of the openings 18. The conductive layer 20 can include one or more layers. Further, the conductive layer 20 can include one or more discrete portions that are electrically connected together or electrically isolated. For example, as shown, e.g., in FIG. 4, the conductive layer 20 includes a first portion 20-1 and a second portion 20-2. The first and second portions 20-1, 20-2 can be formed separately and disposed on the first major surface 14 of the substrate 12 as discrete portions, or formed as a unitary layer adjacent to the first major surface and patterned using any suitable technique or techniques.

The conductive layer 20 can include any suitable conductive material or materials, e.g., titanium, copper, silver, gold, nickel, aluminum, niobium, etc. Further, the conductive layer 20 can take any suitable shape or shapes and have any suitable dimensions. The conductive layer 20 can be disposed on the first major surface 14 of the substrate 12 using any suitable technique or techniques, e.g., vapor deposition, chemical vapor deposition, ink jet printing, plating, etc. In one or more embodiments, the conductive layer 20 can include a foil that is disposed on the first major surface 14 of the substrate 12 as a sheet of material and then patterned using any suitable technique or techniques.

The conductive layer 20 can be hermetically sealed to the first major surface 14 of the substrate 12 using any suitable technique or techniques, e.g., diffusion bonding, laser-assisted diffusion bonding, adhering, mechanically fastening, brazing, etc.

For example, the conductive layer 20 can be hermetically sealed to the first major surface 14 of the substrate 12 using one or more of the diffusion bonding techniques described in co-owned and co-filed U.S. Pat. No. 10,124,559 to Sandlin et al. and entitled KINETICALLY LIMITED NANO-SCALE DIFFUSION BOND STRUCTURES AND METHODS. In one or more embodiments, electromagnetic radiation (e.g., light) can be directed through the substrate 12 from its second major surface 16 and focused on a region between the first major surface 14 of the substrate 12 and the conductive layer 20. Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 2000 nm. For example, laser light can include UV light, visible light, IR light, and combinations thereof. The UV light can be provided by a UV laser that has any suitable wavelength or range of wavelengths and any suitable pulse width. In one or more embodiments, a UV laser can be utilized to provide light having a wavelength in a range of 100-400 nm and a pulse width in a range of 1-100 ns. In one or more embodiments, the materials for the substrate 12 and the conductive layer 20, and the power level and wavelength of the light used may be selected such that the light may not directly damage, ablate, warp, or cut the substrate and the housing, and such that the substrate and the housing retain their bulk properties.

Figure 5:
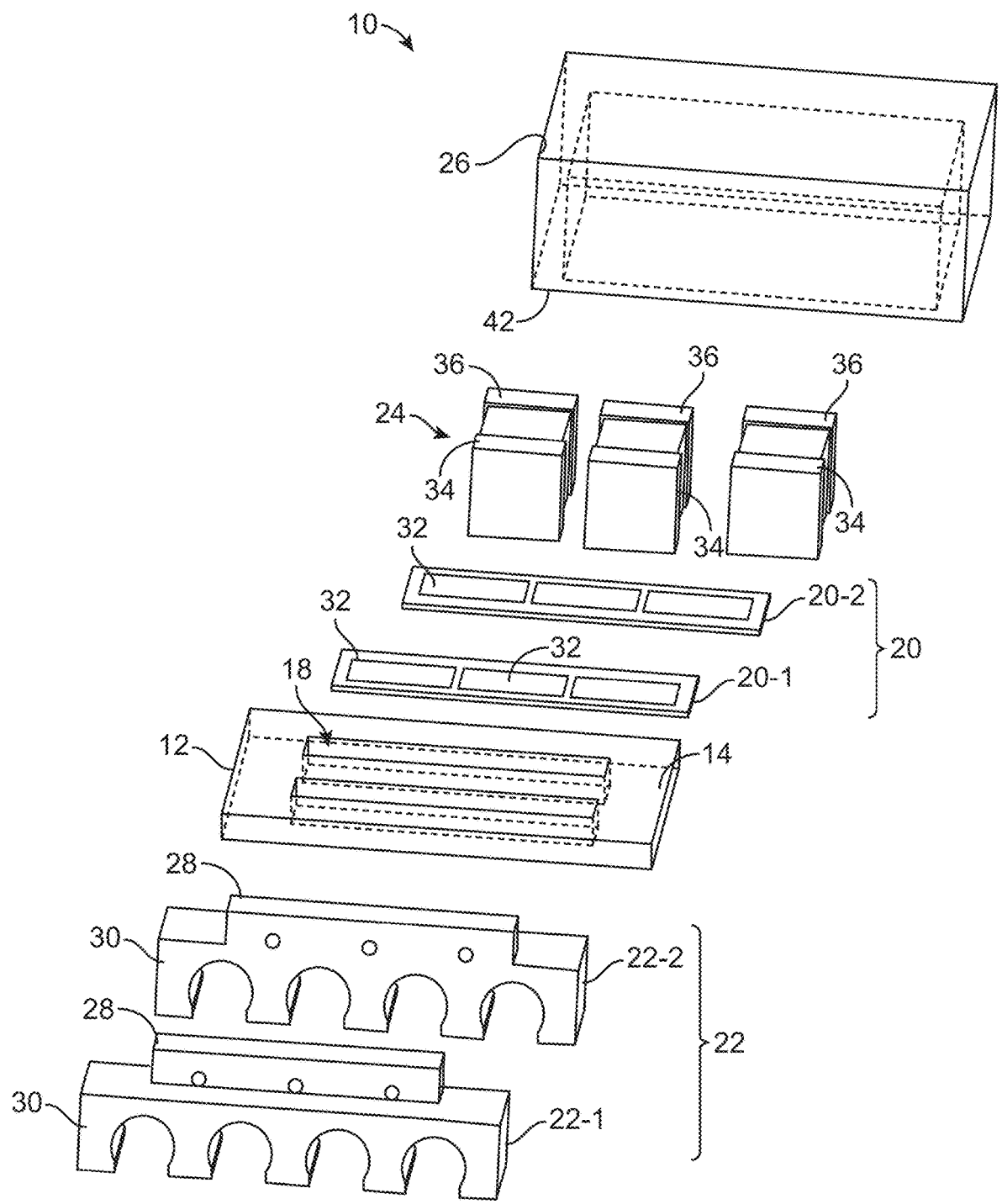
FIG. 5 is a schematic exploded view of the electronic package of FIG. 1.

In general, electromagnetic radiation can be provided by any suitable laser or laser system. For example, the laser may generate electromagnetic radiation having a relatively narrow set of wavelengths (e.g., a single wavelength). In one or more embodiments, the electromagnetic radiation emitted by the laser may form a collimated beam that may not be focused on a particular point. In one or more embodiments, the electromagnetic radiation emitted by the laser may be focused on a focal point at a region between the first major surface 14 of the substrate 12 and the conductive layer 20 to generate a laser bond 2 (FIG. 5).

Although the laser may provide electromagnetic radiation that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., Ti sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat, Gaussian, or other suitable spatial energy profile.

In one or more embodiments, the bond 2 can be a bond line or lines that can be formed between the conductive layer 20 and the substrate 12 such that the conductive layer is hermetically sealed to the substrate. The bond line 2 can take any suitable shape or shapes. For example, the bond line 2 can form a closed shape in a plane parallel to the first major surface 14 of the substrate 12 such that the bond surrounds opening 18. As used herein, the term "closed shape" means that the shape is entirely enclosed such that its perimeter is unbroken and continuous. Any suitable closed shape or shapes can be formed by the bond line 2, e.g., elliptical, rectilinear, triangular, polygonal, etc.

In one or more embodiments, the bond 2 between the conductive layer 20 and the first major surface 14 can be a bonded region that surrounds one or more openings 18. The bonded region can take any suitable shape or combination of shapes. In one or more embodiments, the bond 2 can include two or more shapes with one shape circumscribing the second shape. For example, the bond 2 can include two or more concentric elliptical bond lines or rings. In such embodiments, the two or more shapes may be isolated so that the shapes do not intersect or overlap. In one or more embodiments, the two or more shapes may intersect or overlap along any suitable portion or portions of the shapes. In one or more embodiments, the bond 2 can include two or more bond lines that together surround one or more openings 18. For example, the bond can include a series of parallel lines that are intersected by two or more lines that are non-parallel to the series of parallel lines.

In one or more embodiments, the bond 2 can include an interfacial layer between the conductive layer 20 and the substrate 12. It should be understood that the thickness of the interfacial layer, is in part, a function of the desired strength of the bond 2 and the thickness of the conductive layer 20 and/or the substrate 12. Therefore, this interfacial layer can have any suitable thickness in a direction normal to the first major surface 14 of the substrate 12. In accordance with one or more example embodiments, a typical thickness of the interfacial layer in a direction normal to the first major surface 14 of the substrate 12 includes a thickness of no greater than 10 nm, 100 nm, 150 nm, 200 nm, 500 nm, 1000 nm, or 10 µm.

Disposed in one or more of the openings 18 are conductor blocks 22. The conductor blocks 22 extend beyond the second major surface 16 of the substrate 12 and are electrically connected to the conductive layer 20. Although depicted as including two conductor blocks 22, the package 10 can include any suitable number of conductor blocks. Further, one or more conductor blocks 22 can be disposed in each opening 18. In the embodiment illustrated in FIGS. 1-5, one conductor block 22 is disposed in each opening 18 of the package 10.

The conductor blocks 22 can include any suitable conductive material or materials, e.g., titanium, tantalum, niobium, zirconium, platinum, or other conductive, biocompatible, and biostable material. Further, the conductor blocks 22 can take any suitable shape or shapes and have any suitable dimensions. In one or more embodiments, one or more conductor blocks 22 can include a weld tab 28 and a wire terminal 30 connected to the tab. The weld tab 28 is inserted into the opening 18 such that it is electrically connected to the conductive layer 20. The weld tab 28 can take a shape and have dimensions that are complementary with the shape and dimensions of the opening 18 such that tab substantially fills a volume of the opening. In one or more embodiments, the weld tab 28 can fill less than the entire volume of the opening 18, and any suitable material can be disposed in the opening to fill space within the opening that is not filled by the tab and provide mechanical support to the tab. For example, an adhesive can be disposed within the opening 18, where the adhesive is adapted to connect the conductor block 22 to the conductive layer 20 and one or more walls of the opening 18 such that the weld tab 28 is mechanically connected to the opening and conductive layer 20 and electrically connected to the conductive layer. In one or more embodiments, the conductor block 22 can be connected to the second major surface 16 using any suitable technique or technique, e.g., an adhesive can be disposed between the conductor block and the second major surface of the substrate.

The wire terminal 30 of one or more of the conductor blocks 22 can take any suitable shape or shapes and have any suitable dimension. In one or more embodiments, the wire terminal 30 is adapted to receive a wire or conductor, e.g., of a coil that is disposed within a housing of an implantable medical device as is further described herein. For example, the wire terminal 30 can include one or more slots 31 that extend through the wire terminal and are adapted to receive a wire or other conductor. In embodiments where the package 10 is utilized with a charging coil (e.g., coil 550 of FIG. 15), the wire terminal 30 can be electrically connected to the coil such that current that is induced in the wire by an electromagnetic field can be directed into the wire terminal. Further, the wire terminal 30 is electrically connected to the weld tab 28. The current from the coil can, therefore, be directed from the wire terminal 30 to the weld tab 28 and subsequently to the conductive layer 20. The wire terminal 30 can be integral with the weld tab 28. In one or more embodiments, the wire terminal 30 and weld tab 28 are manufactured separately and connected together using any suitable technique or techniques.

The package 10 further includes the one or more electronic devices 24 that can be disposed adjacent to the first major surface 14 of the substrate 12 and electrically connected to the conductive layer 20. As used herein, the phrase "adjacent to the first major surface" means that an element or component is disposed closer to the first major surface 14 of the substrate 12 than to the second major surface 16 of the substrate. In one or more embodiments, one or more of the electronic devices 24 can be disposed on the conductive layer 20. In one or more embodiments, one or more additional conductive layers, contacts, or pads can be disposed between one or more of the electronic devices 24 and the conductive layer 20. For example, conductive pads 32 (FIG. 4) can be disposed between one or more of the electronic devices 24 and the conductive layer 20. The conductive pads 32 can be electrically connected to one or more electronic devices 24 and the conductive layer 20. Such conductive pads 32 can be disposed between one or more electronic devices 24 and the conductive layer 20 using any suitable technique or techniques. Device contacts 25 (FIG. 1) of electronic devices 24 can be electrically connected to the contact pads 32 of conductive layer 20 using any suitable technique or techniques.

The package 10 can include any suitable number of electronic devices 24. Further, the electronic devices 24 can include any suitable electronic device or component, e.g., capacitors, resistors, diodes, integrated circuits, controllers, processors, sensors (e.g., temperature sensor), batteries, etc. The package 10 can include any combination of electronic devices 24. In one or more embodiments, two or more electronic devices 24 can be electrically connected by conductive layer 20 or other conductors.

In one or more embodiments, each of the electronic devices 24 can include one or more terminals that can be electrically connected to the conductive layer 20. For example, as shown in FIG. 5, each electronic device includes a first terminal 34 and a second terminal 36. The first terminal 34 can be electrically connected to the first portion 20-1 of the conductive layer 20, and the second terminal 36 of the device 24 can be electrically connected to the second portion 20-2 of the conductive layer. The first terminal 34 of the device 24 can be electrically connected to the first conductor block 22-1 via the first portion 20-1 of the conductive layer 20, and the second terminal 36 can be electrically connected to second conductor block 22-2 via the second portion 20-2 of the conductive layer. Current can, therefore, flow from a coil connected to the conductor blocks 22 between the first terminal 34 and the second terminal 36 of at least one of the electronic devices 24.

Disposed over the one or more electronic devices 24 and the substrate 12 is the cover 26. The cover 26 can include any suitable material or materials. In one or more embodiments, the cover 26 is a nonconductive cover that includes one or more nonconductive material or materials, e.g., glass, sapphire, ceramic, or other, nonconductive, biocompatible, biostable material. Further, the cover 26 can be manufactured using any suitable technique or techniques, e.g., molding, etching, laminating, bonding, laser-assisted bonding, co-fired ceramic sintering, hot forming of glass, etc.

The cover 26 can take any suitable shape or shapes and have any suitable dimensions. In one or more embodiments, a recessed surface 38 of the cover 26 forms a cavity 40 of the cover. The cavity 40 can have any suitable dimensions. In one or more embodiments, the electronic devices 24 are disposed within the cavity 40 of the cover 26 when the cover is sealed to the substrate 12.

The cover 26 can be sealed to the substrate 12 using any suitable technique or techniques, e.g., diffusion bonding, laser assisted diffusion bonding, adhering, mechanically connecting, brazing, welding of weld rings, etc. For example, any suitable diffusion bonding technique or techniques can be utilized to connect the cover 26 to the substrate 12, e.g., the same diffusion bonding techniques described herein regarding bonding of the conductive layer 20 to the substrate 12. A bond 4 (FIG. 1) can be formed between an edge 42 of the cover 26 and the first major surface 14 of the substrate 12. In one or more embodiments, the cover 26 is hermetically sealed to the substrate 12. In one or more embodiments, an interfacial layer can be disposed between the cover 26 and the first major surface 14 of the substrate 12 as is further described herein regarding the interfacial layer disposed between the conductive layer 20 and the first major surface 14 of the substrate 12.

Figure 6:
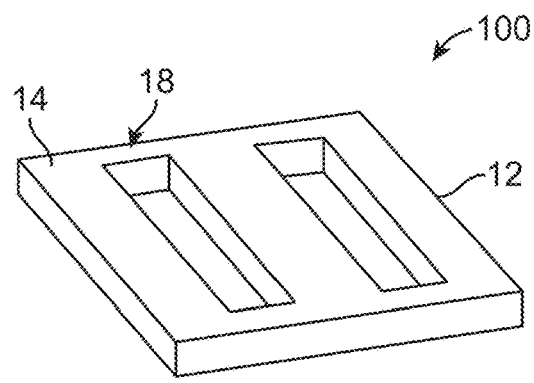
FIG. 6 is a schematic perspective view of one element of a method of making the electronic package of FIG. 1.

Any suitable technique or techniques can be utilized to form the package 10 of FIGS. 1-5. For example, FIGS. 6-10 are various perspective views of one embodiment of a method 100 of forming the package 10. Although described in regard to package 10, the method 100 can be utilized to form any suitable electronic package. In FIG. 6, one or more openings 18 can be disposed through the nonconductive substrate 12 using any suitable technique or techniques, e.g., laser drilling. Any suitable number of openings 18 can be disposed through the substrate 12. In a wafer-to-wafer bonding process, the openings 18 for a plurality of electronic packages 10 can be disposed through a nonconductive substrate wafer.

Figure 7:
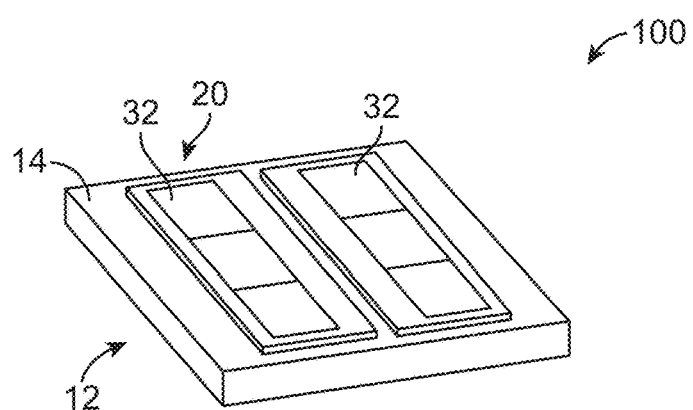
FIG. 7 is a schematic perspective view of another element of the method of FIG. 6.

In FIG. 7, the conductive layer 20 can be disposed adjacent to the first major surface 14 of the substrate 12 and over the openings 18 using any suitable technique or techniques, e.g., vapor deposition. In one or more embodiments, the conductive layer 20 is disposed on the first major surface 14 of the substrate 12. The conductive layer 20 can be hermetically sealed to the first major surface 14 of the substrate 12 and over the openings 18 using any suitable technique or techniques, e.g., diffusion bonding. Further, in one or more embodiments, one or more conductive pads 32 can be disposed on the conductive layer 20 using any suitable technique or techniques. In one or more embodiments, the conductive layer 20 can be patterned using any suitable technique or techniques.

Figure 8:
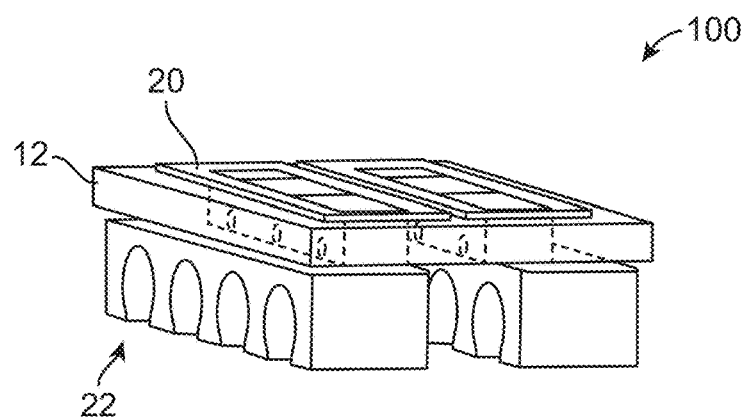
FIG. 8 is a schematic perspective view of another element of the method of FIG. 6.

As shown in FIG. 8, the method 100 further includes disposing one or more conductor blocks 22 in the openings 18 such that the conductor blocks extend beyond the second major surface 16 of the substrate 12, where the conductor blocks are electrically connected to the conductive layer 20. Any suitable technique or techniques can be utilized to dispose the conductor blocks 22 in the openings 18. In one or more embodiments, the weld tab 28 of each conductor block 22 can be inserted into the opening 18 such that the tab is electrically connected to the conductive layer 20. The conductor blocks 22 are electrically connected to the conductive layer 20 using any suitable technique or techniques. In one or more embodiments, the conductor blocks 22 are mechanically connected to the substrate 12 using any suitable technique or techniques, e.g., each conductor block can be mechanically connected to the walls of the opening 18 or to the second major surface 16 of the substrate 12 with an adhesive.

Figure 9:
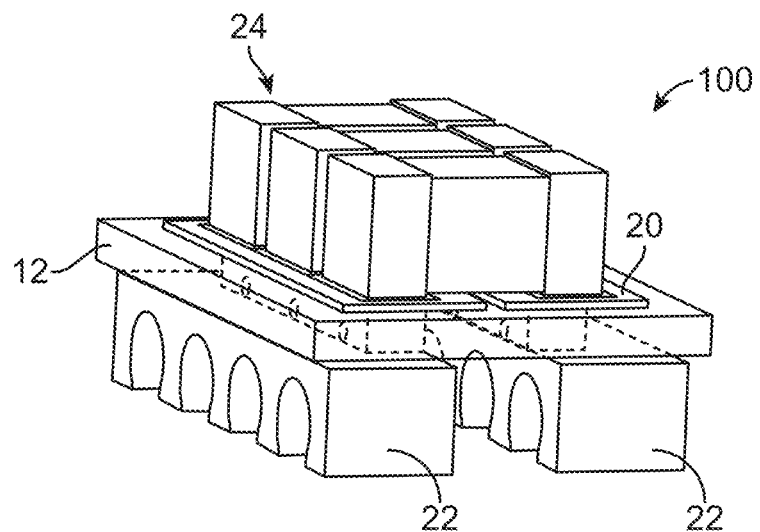
FIG. 9 is a schematic perspective view of another element of the method of FIG. 6.

In FIG. 9, one or more electronic devices 24 can be disposed adjacent to the first major surface 14 of the substrate 12 using any suitable technique or techniques. The electronic devices 24 can be electrically connected to the conductive layer 20 using any suitable technique or techniques, e.g., device contacts 25 can electrically connect the devices to the conductive layer. In one or more embodiments, the electronic devices 24 can, therefore, be electrically connected to the conductor blocks 22 via the conductive layer 20.

Figure 10:
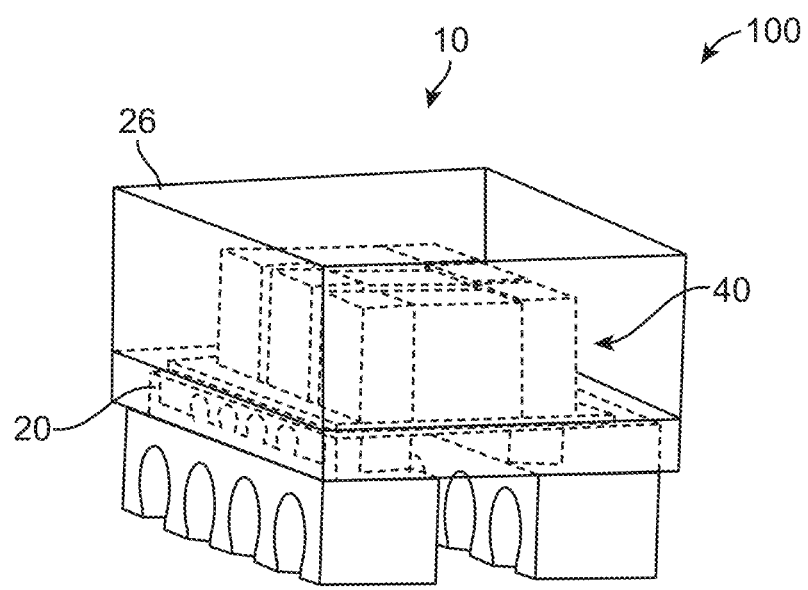
FIG. 10 is a schematic perspective view of another element of the method of FIG. 6 with the cover and the substrate of the package made transparent for clarity.

As shown in FIG. 10, the nonconductive cover 26 can be disposed over the electronic devices 24 and the conductive layer 20 using any suitable technique or techniques such that the electronic devices and conductive layer are disposed within the cavity 40 of the cover. In wafer-to-wafer bonding processes, a nonconductive cover wafer can be disposed over the electronic devices 24 and the conductive layer 20. The cover 26 can also be sealed to the nonconductive substrate 12 using any suitable technique or techniques (e.g., diffusion bonding) to form the electronic package 10. In one or more embodiments, the cover 26 is hermetically sealed to the nonconductive substrate 12. For wafer processing, the nonconductive cover wafer can be hermetically sealed to the nonconductive substrate wafer, and the wafers can be singulated using any suitable technique or techniques to form a plurality of electronic packages 10, e.g., mechanically sawing the nonconductive cover wafer and the nonconductive substrate wafer to form one or more electronic packages.

Figure 11:
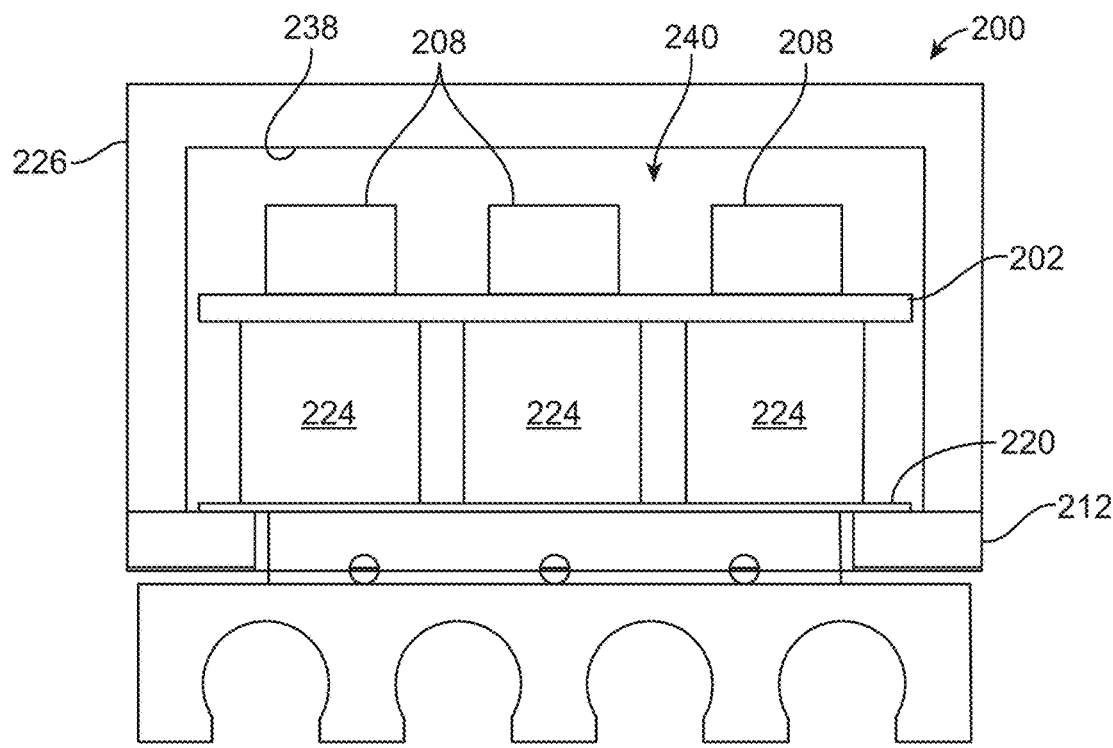
FIG. 11 is a schematic cross-section view of another embodiment of an electronic package.

FIG. 11 is a schematic cross-section view of another embodiment of an electronic package 200. All of the design considerations and possibilities described herein regarding the electronic package 10 of FIGS. 1-5 apply equally to the electronic package 200 of FIG. 11. One difference between package 200 of FIG. 11 and package 10 of FIGS. 1-5 is that package 200 includes a second substrate 202 that faces substrate 212 and additional electronic devices 208 disposed on the substrate and electrically connected to conductive layer 220 using any suitable technique or techniques. The second substrate 202 can include any suitable substrate, e.g., substrate 12 of FIGS. 1-5. The second substrate 202 can also include a conductive layer disposed on one or both of its major surfaces. The additional electronic devices 208 can include any suitable electronic devices, e.g., the same electronic devices described herein regarding electronic devices 24 of FIGS. 1-5. Electronic devices 224 are disposed between the substrate 212 and the second substrate 202. Further, one or more of the electronic devices 224 can be electrically connected to a conductive layer of the second substrate 202 and conductive layer 220 of substrate 212. The substrate 212, electronic devices 224, second substrate 202, and additional electronic devices 208 can be disposed within a cavity 240 of cover 226 that is defined by a recessed surface 238 of the cover. As with electronic package 10 of FIGS. 1-5, cover 226 can be hermetically sealed to substrate 212 using any suitable technique or techniques.

Figure 12:
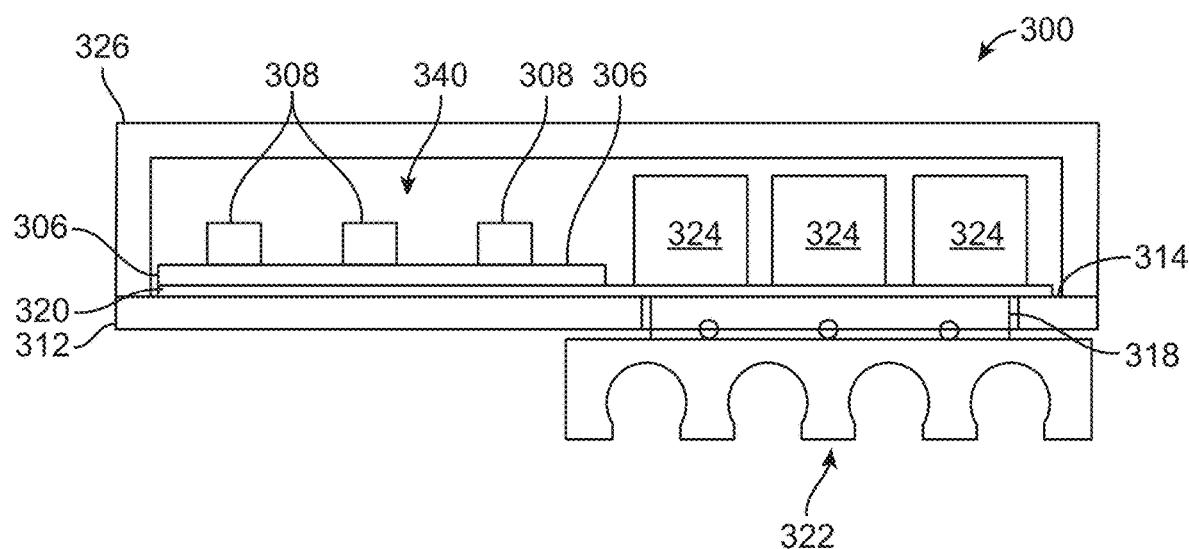
FIG. 12 is a schematic cross-section view of another embodiment of an electronic package.

Another embodiment of an electronic package 300 is illustrated in FIG. 12. All of the design considerations and possibilities described herein regarding electronic package 10 of FIGS. 1-5 and electronic package 200 of FIG. 11 apply equally to electronic package 300 of FIG. 12. One difference between package 300 and packages 10 and 200 is that additional electronic devices 308 of package 300 can be disposed on conductive layer 320 or on a second substrate 306 that is disposed on the conductive layer. The additional electronic devices 308 can be disposed adjacent to a first major surface 314 of substrate 312. In one or more embodiments, the additional electronic devices 308 are not disposed over an opening disposed through the substrate 312. To accommodate the electronic devices 308, cavity 340 of housing 326 has a volume that allows for the additional electronic devices to be disposed within the cavity along with electronic devices 324. Additional electronic devices 308 can be electrically connected to the conductive layer 320 using any suitable technique or techniques, e.g., the same techniques described herein regarding electrical connection of electronic devices 24 to conductive layer 20 of package 10. Further, additional electronic devices 308 can be electrically connected to devices 324 via the conductive layer 320 or one or more additional conductors disposed within the cavity 340. The additional electronic devices 308 can include any suitable electronic devices. Further, the package 300 can include any suitable number of additional electronic devices 308, e.g., the same electronic devices described herein regarding electronic devices 24 of FIGS. 1-5. Such additional electronic devices 308 may not be directly connected to conductor blocks 322 that are disposed within openings 318 of substrate 312.

Figure 13:
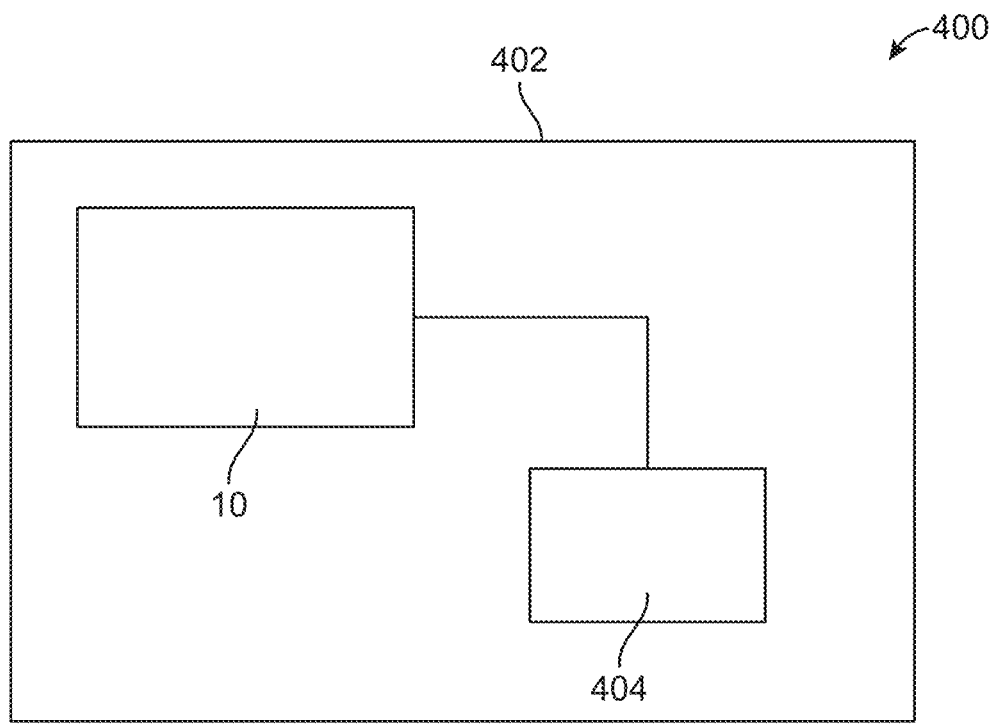
FIG. 13 is a schematic plan view of one embodiment of a device that includes the electronic package of FIG. 1.

The various embodiments of electronic packages described herein can be utilized in any suitable device or system. For example, FIG. 13 is a schematic plan view of one embodiment of a device 400. The device can be any suitable device 400, e.g., an implantable medical device. Such implantable medical device can include any suitable implantable medical device, e.g., defibrillator, LVAD, neurostimulator, pacemaker, drug pump, etc. Further, the disclosed embodiments of implantable medical devices can be utilized with any suitable system or systems. For example, one or more embodiments of implantable medical devices can be utilized with a wireless energy transfer system, e.g., one or more of the systems described in U.S. Pat. No. 10,143,788 B2, entitled TRANSCUTANEOUS ENERGY TRANSFER SYSTEMS.

For example, the device 400 can be an implantable medical device that includes a housing 402 and electronic package 10 of FIGS. 1-5 disposed within the housing. Although described in regard to package 10 of FIGS. 1-5, the device 400 can include any suitable electronic package. In one or more embodiments, one or more additional electronic components or devices 404 can be disposed within the housing 402. Such additional components 404 can be electrically connected to the electronic package 10 using any suitable technique or techniques. The housing 402 can include any suitable housing that can take any suitable shape or shapes and have any suitable dimensions. Further, the housing 402 can include any suitable material or materials, e.g., metallic material such as titanium and steel, polymeric materials such as polyurethane, inorganic materials such as ceramics, glass, or combinations thereof.

Figure 14:
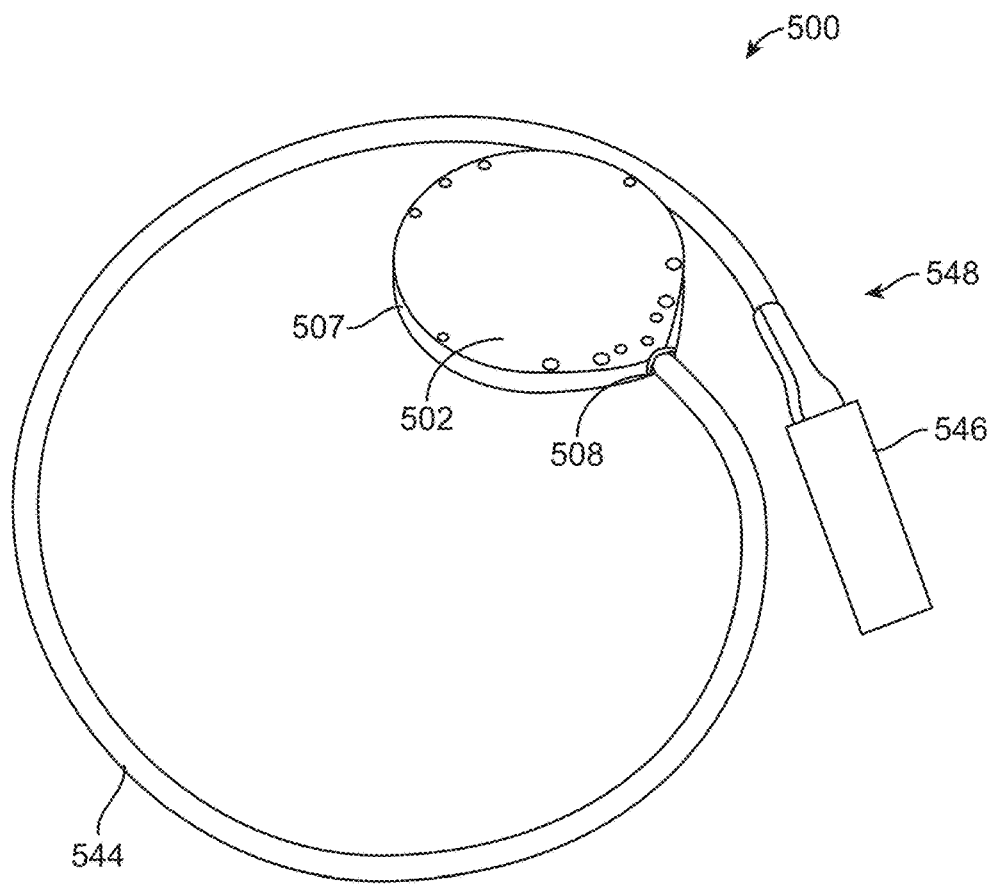
FIG. 14 is a schematic perspective view of one embodiment of an implantable medical device.
Figure 15:
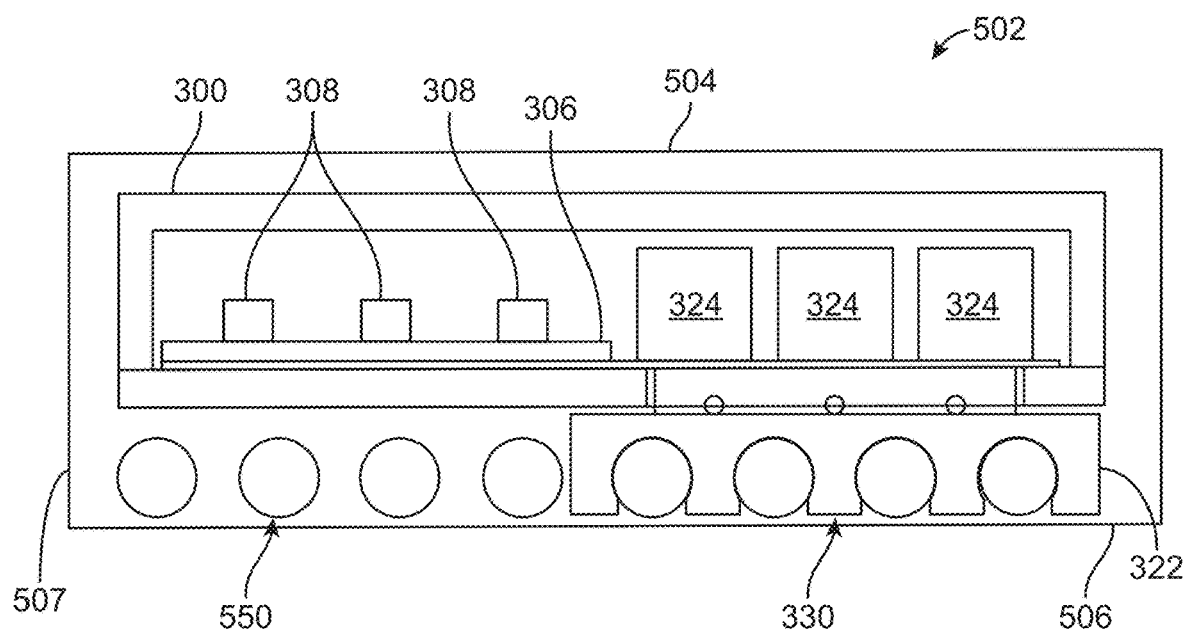
FIG. 15 is a schematic cross-section view of a housing of the implantable medical device of FIG. 14.

The device 400 can include any suitable device or devices. For example, FIGS. 14-15 are various views of another embodiment of an implantable medical device 500. The device 500 can be a part of a wireless energy transfer system that can also include an external component that can provide an electromagnetic field to the implantable medical device 500 such that electromagnetic energy can be transferred from the external component to the medical device 500 to provide energy to one or more electronic components are packages disposed within a housing 502 of the device or electrically connected to the device by cable 544. The device 500 includes a housing 502 having a first major surface 504, a second major surface of 506, a sidewall 507 that extends between the first major surface and the second major surface, and a port 508 disposed in the sidewall. The device 500 also includes electronic package 300 of FIG. 12 disposed within the housing 502. Although described in regard to package 300 of FIG. 12, the device 500 can include any suitable electronic package described herein, e.g., package 10 of FIGS. 1-5. The cable 544 is electrically connected to the electronic package 300 and extends through the port 508.

The housing 502 can take any suitable shape or shapes and have any suitable dimensions. Further, the housing 502 can include any suitable material or materials, e.g., silicone, ceramic, polyurethane, or metal. In one or more embodiments, the housing 502 includes a nonconductive matrix that encases the electronic package 300. Any suitable material or materials can be utilized for the nonconductive matrix, e.g., polymers such as polyurethane, PEEK, silicone, polysulfone, epoxy, or any nonconductive, biocompatible, biostable material. In one or more embodiments, the housing 502 can further include a shell that surrounds the polymer matrix.

The first and second major surfaces 504, 506 of the housing 502 can have any suitable dimensions and take any suitable shape or shapes. In one or more embodiments, at least one of the first major surface 504 or the second major surface 506 can take a planar shape. In one or more embodiments, at least one of the first major surface 504 or the second major surface 506 can take a curved shape.

The cable 544 can include any suitable material or materials, e.g., urethane, silicone, carbothane, MP35N, MP35N/ silver core, etc. The cable 544 can include one or more conductors disposed within a protective sheath or covering. Such conductors can be electrically connected to the electronic device 300 using any suitable technique or techniques. The cable 544 can include any suitable number of conductors. Further, the cable 544 can have any suitable dimensions. The cable 544 can also have any suitable cross-sectional shapes, e.g., elliptical, rectangular, etc.

Although depicted as being connected to a single electronic package 300, the cable 544 can be connected to two or more electronic components disposed within the housing 502 of the device 500. Further, the cable 544 can include a connector 546 electrically connected to cable end 548. Such connector 546 can include any suitable connector that is adapted to connect the electronic package 300 disposed within the housing 502 to any suitable component or element, e.g., a pump.

The device 500 can also include a coil 550 disposed in any suitable location on or within the housing 502. The coil 550 can include any suitable material or materials and take any suitable shape or shapes. Further, the coil 550 can have any suitable dimensions and include any desired number of windings. In one or more embodiments, the coil 550 can be electrically connected to at least one of the electronic package 300 or the cable 544 using any suitable technique or techniques.

The coil 550 can be electrically connected to one or more conductor blocks 322 of the electronic package 300 using any suitable technique or techniques. In one or more embodiments, one or more of the wires of the coil 550 can be disposed within cleats 330 of conductor blocks 322 to provide electrical connections between electronic components 324 and the coil via conductor blocks 322. Further, in one or more embodiments, the coil 550 can also be electrically connected to additional electronic devices 308 using any suitable technique or techniques. In general, current induced in the coil 550 by an electromagnetic field applied by an external component of an energy transfer system can charge electronic components 324 thereby storing energy within the package 300 or elsewhere within the body. Such energy can be utilized to provide power to additional electronic devices 308.

Figure 17:
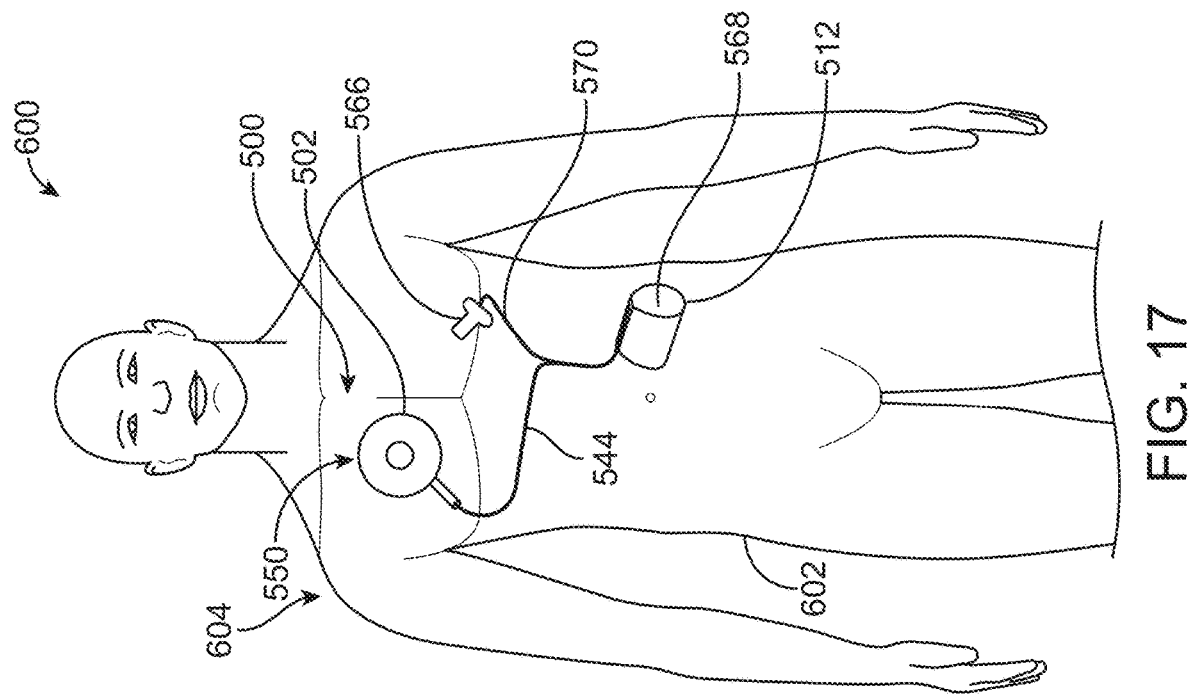
FIG. 17 is a schematic plan view of internal components of the wireless energy transfer system of FIG. 16 and the implantable medical device of FIG. 14.
Figure 16:
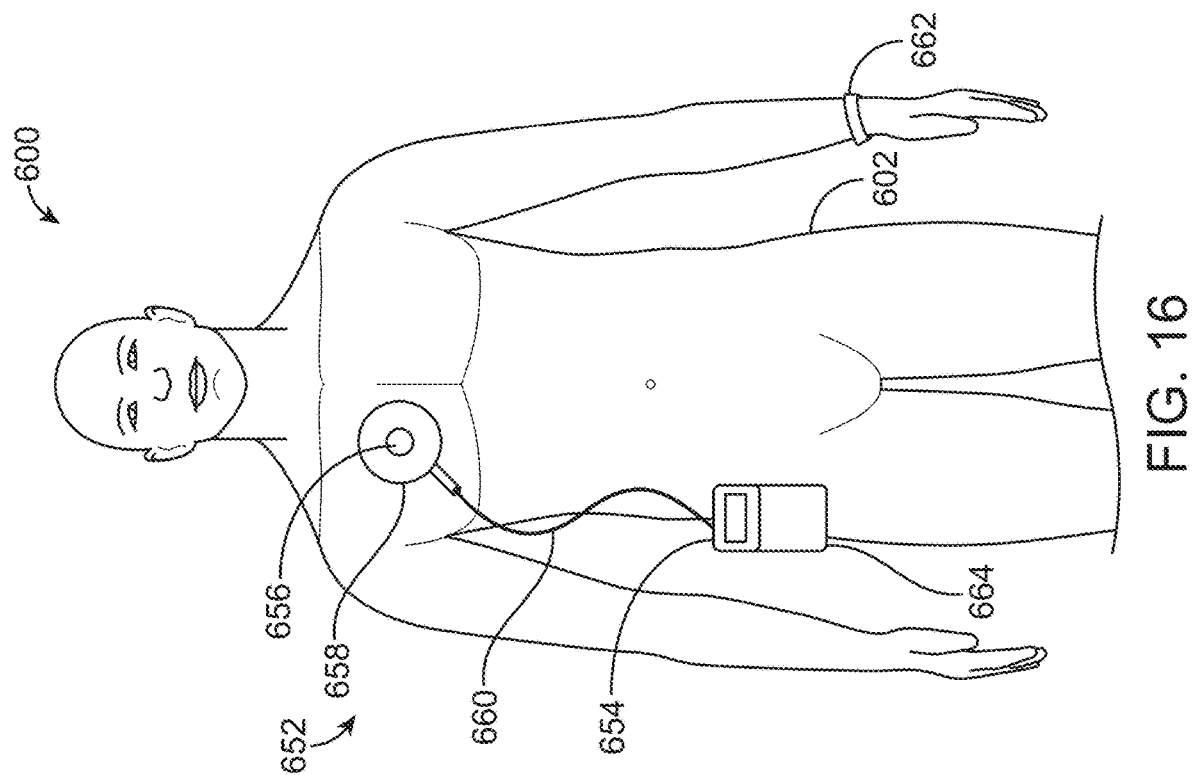
FIG. 16 is a schematic plan view of external components of a wireless energy transfer system.

The various embodiments of implantable medical devices described herein can be utilized with any suitable system. For example, FIGS. 16-17 are schematic views of one embodiment of a wireless energy transfer system 600. The system 600 includes the implantable medical device 500 of FIGS. 14-15 and external components 652. In FIG. 16, the external components 652 of the system 600 are illustrated, and in FIG. 17, the implantable medical device 500 of the system is illustrated as being implanted within a body 602 of a patient 604. The external components 652 can include an external module 654 and a primary coil 656. In one or more embodiments, the primary coil 656 can be disposed in a separate housing 658 from the external module 654. The external module 654 can be located in any suitable location relative to the patient's body 602, e.g., around the patient's hip (e.g., in a pocket of the patient's clothing, mounted to a belt of the patient, etc.), and the primary coil 656 can be located in any suitable location relative to the patient's body 602, e.g., on the patient's chest and secured in place by a garment worn by the patient, such as a sling or vest. The external module 654 and primary coil 656 are further connected to each other by a wire 660. Also shown in FIG. 16 is a clinical monitor 662, which can be worn, e.g., on the patient's wrist. In other examples, the clinical monitor 662 can be located elsewhere, such as in the external module, or in the patient's smartphone, or not on the patient altogether.

In the embodiment illustrated in FIG. 16, an external battery, and external electronics (not shown) can be disposed in a housing 664 of the external module 654. In one or more embodiments, the external battery may be disposed in a separate housing (e.g., separately mounted to the outside of the patient) and wired to the external module 654.

Although the system 600 includes electronic device 500 of FIGS. 14-15, the system can include any suitable electronic device or package described herein, e.g., electronic package 10 of FIGS. 1-5. As illustrated in FIG. 17, the implantable medical device 500 can include the coil 550 (i.e., secondary coil 550) disposed within the housing 502, a pump 566, and an electronic module 568 electrically connected to the housing and the pump. In one or more embodiments, each of the housing 502, the pump 566, and the electronic module 568 can be disposed in a separate housing and dispersed throughout the patient's body 602 to accommodate the anatomy of the patient. For instance, in the embodiment illustrated in FIG. 17, the housing 502 is mounted in the patient's chest. In one or more embodiments, the housing 502 can be mounted to the patient's rib, back, abdomen, or muscle in any subcutaneous plane.

The housing 502 is electrically connected to the electronic module 568 by the cable 544, and the pump 566 is electrically connected to the electronics module 568 by a second cable 570. The pump 566 can be connected, e.g., to a heart of the patient. Although not shown, the implantable medical device 500 can also include an implanted battery disposed in any suitable location within the patient's body 602. In one or more embodiments, the implanted battery is disposed within a housing 512 of the electronics module 568. In one or more embodiments, the implanted battery may be separately housed, and an additional wire may connect the electronics module 568 to the implanted battery.

The secondary coil 550 is disposed within the housing 502 of the implantable medical device 500 and is adapted to be electrically coupled to the primary coil 656. For example, the secondary coil 550 can be adapted to be inductively coupled to the primary coil 656. Positioning of the secondary coil 550 within the patient 604 can be done in such a manner that makes mounting the primary coil 656 in proximity to the secondary coil easy for the patient. For instance, the secondary coil 550 can be positioned close to the skin of the patient 604. Moreover, the secondary coil 550 can be positioned close to a relatively flat part of the patient's body 602 to make mounting the primary coil 656 easier. In the embodiment illustrated in FIG. 17, the secondary coil 550 disposed within the housing 502 is positioned close to the front of the patient's chest such that mounting the primary coil 656 to the patient's chest places the primary coil proximate the secondary coil. In those examples where the housing 502 is mounted to the patient's rib, back, or abdomen, the secondary coil 550 can similarly be located close to the patient's skin, such that the primary coil 656 can be mounted in close proximity.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:
1. An electronic package comprising:
a nonconductive substrate comprising a first major surface, a second major surface, and an opening disposed through the substrate between the first major surface and the second major surface;

a conductive layer hermetically sealed to the first major surface of the substrate and over the opening;

a conductor block disposed in the opening and extending beyond the second major surface of the substrate, wherein the conductor block is electrically connected to the conductive layer;

an electronic device disposed adjacent to the first major surface of the substrate and electrically connected to the conductive layer; and a nonconductive cover disposed over the electronic device and the nonconductive substrate and hermetically sealed to the substrate, wherein the electronic device is disposed within a cavity of the cover.

2. The package of claim 1, further comprising a conductive pad disposed between the electronic device and the conductive layer, wherein the conductive pad is electrically connected to the electronic device and the conductive layer.

3. The package of claim 1, wherein the electronic device comprises a capacitor.

4. The package of claim 1, wherein the conductor block comprises a weld tab and a wire terminal connected to the weld tab, wherein the weld tab is inserted into the opening of the nonconductive substrate, wherein the wire terminal is adapted to receive a wire.

5. The package of claim 1, wherein the nonconductive cover is diffusion bonded to the nonconductive substrate.

6. The package of claim 1, further comprising an adhesive disposed within the opening of the nonconductive substrate and adapted to connect the conductor block to the conductive layer and one or more walls of the opening.

7. An implantable medical device comprising:
a housing; and
an electronic package disposed within the housing, the electronic package comprising:
a nonconductive substrate comprising a first major surface, a second major surface, and an opening disposed through the substrate between the first major surface and the second major surface;
a conductive layer hermetically sealed to the first major surface of the substrate and over the opening;
a conductor block disposed in the opening and extending beyond the second major surface of the substrate, wherein the conductor block is electrically connected to the conductive layer;
an electronic device disposed adjacent to the first major surface of the substrate and electrically connected to the conductive layer; and
a nonconductive cover disposed over the electronic device and the nonconductive substrate and hermetically sealed to the substrate, wherein the electronic device is disposed within a cavity of the cover.

8. The device of claim 7, further comprising a coil disposed within the housing and electrically connected to the electronic package.

9. The device of claim 7, further comprising a cable extending through a port in the housing and electrically connected to the electronic package.

10. The device of claim 7, wherein the housing comprises a nonconductive matrix that encases the electronic package.

11. The device of claim 10, wherein the housing further comprises a shell surrounding the nonconductive matrix.

12. The device of claim 11, wherein the shell comprises a titanium layer disposed on the nonconductive matrix.

13. The device of claim 11, wherein the shell comprises a foil layer disposed on the nonconductive matrix.

14. The device of claim 11, wherein the shell comprises silicone.

15. The device of claim 7, further comprising an additional electronic component disposed within the housing and electrically connected to the electronic package.

16. A wireless energy transfer system comprising the implantable medical device of claim 7.

17. A method comprising:
disposing an opening through a nonconductive substrate, wherein the opening extends between a first major surface and a second major surface of the nonconductive substrate;
hermetically sealing a conductive layer to the first major surface of the substrate and over the opening;
disposing a conductor block in the opening such that it extends beyond the second major surface of the substrate, wherein the conductor block is electrically connected to the conductive layer;
disposing an electronic device adjacent to the first major surface of the nonconductive substrate, wherein the electronic device is electrically connected to the conductive layer;
disposing a nonconductive cover over the electronic device and the conductive layer, wherein the electronic device is disposed within a cavity of the cover; and
hermetically sealing the nonconductive cover to the nonconductive substrate to form an electronic package.

18. The method of claim 17, further comprising disposing a conductive pad on the conductive layer prior to disposing the electronic device such that the conductive pad is between the electronic device and the conductive layer, wherein the conductive pad is electrically connected to the electronic device and the conductive layer.

19. The method of claim 17, further comprising disposing the electronic package within a polymer matrix.

20. The method of claim 19, further comprising disposing a shell on the polymer matrix.

* * * * *